:::: {.page}
United States Patent
Weigand et al.

(12) United States Patent
(10) Patent No.: US 8,013,174 B2
(45) Date of Patent: Sep. 6, 2011

(54) PHOTOCHROMIC SPIRODIHYDROPHENANTHROPYRANS

(75) Inventors: Udo Weigand, Munich (DE); Manfred Melzig, Wessling (DE); Yven Rohlfing, Munich (DE)

(73) Assignee: Rodenstock GmbH, Munich (DE)

( * ) Notice: Subject to any disclaimer, the term of this patent is extended or adjusted under 35 U.S.C. 154(b) by 681 days.

(21) Appl. No.: 12/118,091

(22) Filed: May 9, 2008

(65) Prior Publication Data
US 2008/0262248 A1 Oct. 23, 2008

Related U.S. Application Data

(63) Continuation of application No. PCT/EP2006/010562, filed on Nov. 3, 2006.

(30) Foreign Application Priority Data

Nov. 10, 2005 (DE) .................. 10 2005 053 986

(51) Int. Cl.
C07D 311/78 (2006.01)
C07D 309/00 (2006.01)
C07D 333/50 (2006.01)
C07D 215/00 (2006.01)
C07D 295/18 (2006.01)

(52) U.S. Cl. ........ 549/384; 549/382; 549/358; 549/357; 549/29; 549/41; 549/332; 549/336; 546/152; 546/173.2; 544/171; 548/147; 548/457

(58) Field of Classification Search ............. 549/384, 549/382, 358, 357, 29, 41, 332, 336; 546/152, 546/173, 2; 544/171; 548/147, 457, 5
See application file for complete search history.

(56) References Cited

U.S. PATENT DOCUMENTS

| | | | |
|---|---|---|---|
| 3,567,605 A | | 3/1971 | Becker |
| 5,514,817 A | * | 5/1996 | Knowles .................. 549/384 |
| 5,558,583 A | | 9/1996 | Shimomura |
| 5,645,767 A | | 7/1997 | Van Gemert |
| 5,674,432 A | * | 10/1997 | Knowles et al. ............ 252/586 |
| 5,698,141 A | | 12/1997 | Kumar |
| 5,723,072 A | | 3/1998 | Kumar |
| 5,955,520 A | | 9/1999 | Heller et al. |
| 6,018,059 A | | 1/2000 | Chan |
| 6,149,841 A | * | 11/2000 | Kumar .................. 252/586 |
| 6,379,591 B1 | | 4/2002 | Breyne |
| 6,426,023 B1 | * | 7/2002 | Breyne et al. ............ 252/586 |
| 6,506,538 B1 | | 1/2003 | Breyne et al. |

(Continued)

FOREIGN PATENT DOCUMENTS

CA 2 390 770 A1 3/2002

(Continued)

OTHER PUBLICATIONS

International Search Report dated Mar. 6, 2007 with English translation (Six (6) pages).

*Primary Examiner* — Andrew D. Kosar
(74) *Attorney, Agent, or Firm* — Crowell & Moring LLP

(57) ABSTRACT

Specific photochromic spirodihydrophenanthropyrans and their use in synthetic resin materials of all kinds, particularly for ophthalmic purposes. The compounds of the invention are photochromic pyran compounds derived from 9,10-dihydrophenanthrene in which at least one of the two carbon atoms at positions 9 and 10 belongs to a further ring system and thus forms a spiro linkage point.

9 Claims, 1 Drawing Sheet

::::

U.S. PATENT DOCUMENTS

| | | |
|---|---|---|
| 2002/0169315 A1 | 11/2002 | Mann et al. |
| 2004/0094753 A1 | 5/2004 | Izumi et al. |

FOREIGN PATENT DOCUMENTS

| | | |
|---|---|---|
| EP | 1 529 780 A1 | 5/2005 |
| JP | 2000-344762 A | 12/2000 |
| WO | WO 96/14596 A1 | 5/1996 |
| WO | WO 98/32037 A1 | 7/1998 |
| WO | WO 99/15518 A1 | 4/1999 |
| WO | WO 01/94336 A1 | 12/2001 |
| WO | WO 02/22594 A1 | 3/2002 |

* cited by examiner

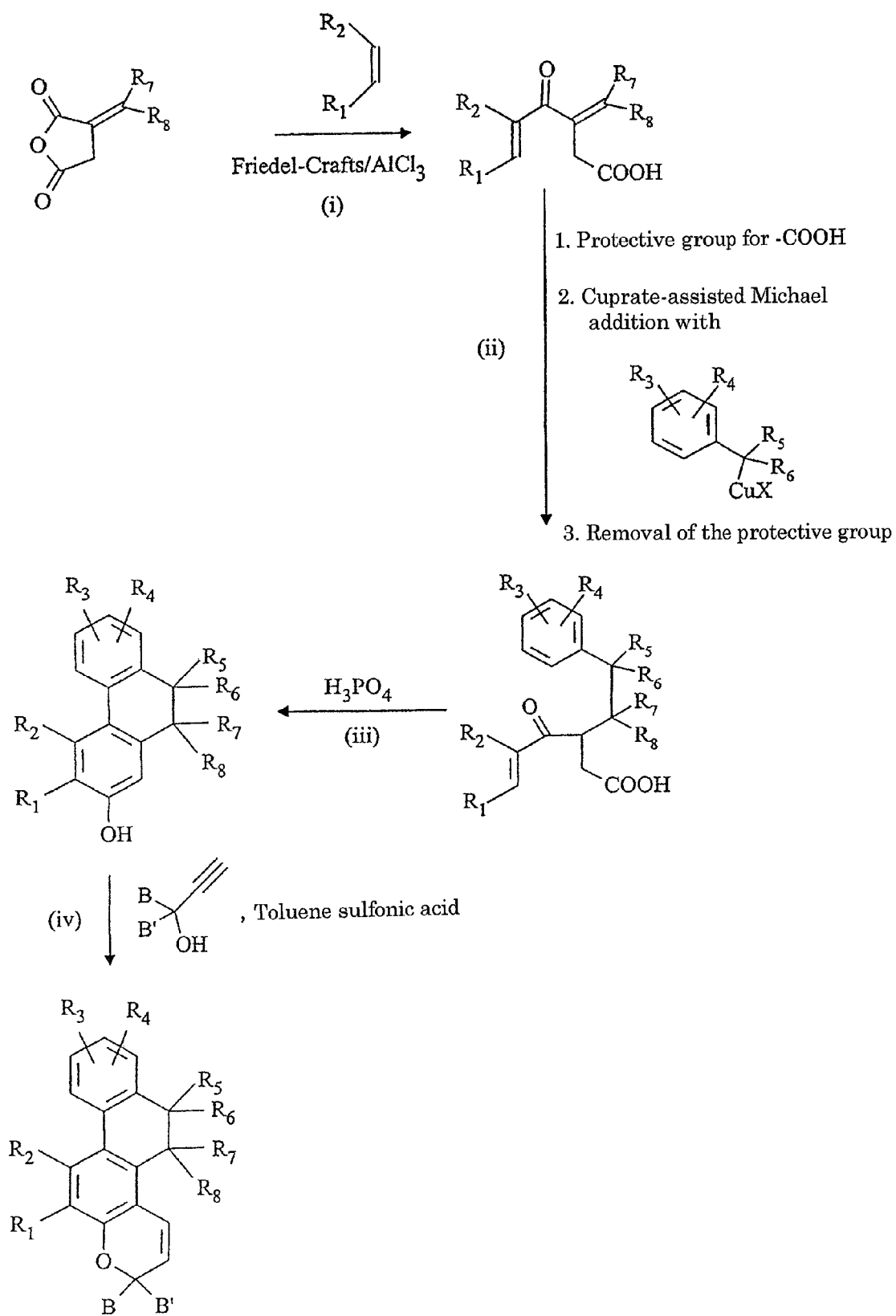

PHOTOCHROMIC SPIRODIHYDROPHENANTHROPYRANS

CROSS REFERENCE TO RELATED APPLICATIONS

This application is a continuation of international patent application no. PCT/EP2006/010562, filed Nov. 3, 2006 designating the United States of America and published in German on May 18, 2007 as WO 2007/054240, the entire disclosure of which is incorporated herein by reference. Priority is claimed based on Federal Republic of Germany patent application no. DE 10 2005 053 986.6, filed Nov. 10, 2005.

BACKGROUND OF THE INVENTION

The present invention relates to specific photochromic spirodihydrophenanthropyrans and to their use in plastics of all kinds, in particular for ophthalmic purposes. The compounds of the invention are photochromic pyran compounds, which are derived from 9,10-dihydrophenanthrene. According to the invention, at least one of the two carbon atoms in position 9 or 10 belongs to an additional ring system and, thus, forms a spiro linkage point.

Different classes of dyes have existed for a long time. When these dyes are irradiated with light of certain wavelengths, in particular solar rays, they change their color reversibly. The reason is due to the fact that light energy causes these dye molecules to change over into an excited state, which they leave again when the supply of energy is interrupted and return to their initial state. These photochromic dyes include a wide variety of pyran systems, which have already been described with different base systems and substituents in the state of the art.

Pyrans, especially naphthopyrans, and larger ring systems, which are derived from said naphthopyrans, are photochromic compounds, which to date have been the object of intensive investigations. Although the first patent was filed already in 1966 (U.S. Pat. No. 3,567,605), compounds, which appear to be suitable for use in spectacle lenses, were not developed until the 1990s. A suitable class of pyran compounds is, for example, the 2,2-diaryl-2H-naphtho[1,2-b]pyrans or the 3,3-diaryl-3H-naphtho[2,1-b]-pyrans, which exhibit different hues, such as yellow, orange or reddish orange, in the excited form.

Other compound classes of photochromic compounds that are of interest include the higher annellated pyrans, which absorb longer wavelengths owing to their larger ring system and produce hues of red, violet and blue. They may be systems, which are derived from either the 2H-naphtho[1,2-b] pyrans or the 3H-naphtho[2,1-b]pyrans and which are produced from the respective naphthopyran systems by annellation on the f side.

Currently the most promising photochromic compounds are diaryl chromenes, in particular naphthopyrans or heterocyclically annellated benzopyrans, which are substituted in position 6 of the benzopyran with a phenyl ring or, more generally, with an aromatic or heteroaromatic ring, which is bridged, in addition, in the position 5 of the benzopyran by means of at least one carbon atom, oxygen atom or nitrogen atom.

If the bridging is produced with just one atom, then the result is a five membered ring, annellated to the benzopyran. Examples for a carbon atom may be found in the U.S. Pat. No. 5,645,767, U.S. Pat. No. 5,723,072 and U.S. Pat. No. 5,955,520; examples for an oxygen atom may be found in the U.S. Pat. No. 6,018,059.

In the U.S. Pat. No. 5,723,072 an unsubstituted, monosubstituted or disubstituted heterocyclic ring on the g, h, i, n, o or p side of the indenonaphthopyran may, in addition, be annellated to the base system. Hence, indeno[1,2-f]naphtho[1,2-b] pyrans with a very large variation of possible substituents are disclosed.

WO 96/14596, WO 99/15518, U.S. Pat. No. 5,645,767, WO 98/32037 and U.S. Pat. No. 5,698,141 disclose photochromic indeno-annellated naphthopyran dyes, derived from 2H-naphtho[1,2-b]pyran, the compositions thereof as well as a method for their production. Moreover, the U.S. Pat. No. 5,698,141 discloses that an unsubstituted, monosubstituted or disubstituted heterocyclic ring on the g, h, i, n, o or p side of the indenonaphthopyran may, in addition, be annellated to this base system. The very extensive list of substituents also includes very specific spiro compounds and, in particular, such systems comprising a spiro heterocyclic group, in which there is a 5 to 8 membered ring, which always contains two oxygen atoms, with the inclusion of the spiro atom at the position 13 of the base system. Another embodiment of the spiro ring is disclosed in the Japanese application 344762/2000.

If this compound is produced through two atoms, the result is an annellated six membered ring with a plurality of possibilities just for C, O and N alone. Compounds with C=O and N—R (lactam bridge) are described in the U.S. Pat. No. 6,379,591. Compounds with an unsubstituted $CH_2$—$CH_2$ bridge as well as an annellated heterocycle in position 7, 8 of the underlying benzopyran are disclosed in the U.S. Pat. No. 6,426,023.

U.S. Pat. No. 6,506,538 describes the carbocyclic analog compounds, where the H atoms in the bridge may be substituted with OH, ($C_1$-$C_6$) alkoxy or where two H atoms at a C atom may be substituted with =O.

If this compound is produced with three atoms, the result is an annellated 7 membered ring with very many variation options because of the insertion of heteroatoms. Compounds with a $CH_2$—$CH_2$—$CH_2$ bridge are described in the U.S. Pat. No. 6,558,583. In this case, too, the H atoms in the bridge may be substituted with OH, ($C_1$-$C_6$) alkyl or ($C_1$-$C_6$) alkoxy, or two hydrogen atoms at a C atom may be substituted with =O. In the event of an identical substitution pattern they absorb shorter wavelengths than the annellated 6 membered rings.

US 2004/0094753 describes both compounds with a bridge comprising 2 as well as 3 atoms. In this case the two atom (carbon) bridge is additionally annellated with a carbocycle and/or heterocycle. The three atom bridge contains three C atoms or two C atoms and one O atom without additional annellation. Both rings may carry a plurality of substituents.

However, the wide variety of photochromic dyes that are available in the state of the art have drawbacks that have a significant negative effect on the wearing comfort of the spectacle wearer when these photochromic dyes are used in ophthalmic sunglass lenses. First of all, the dyes have an inadequate long-wave absorption in the excited as well as in the unexcited state. Secondly the temperature sensitivity with respect to the darkening is too high. At the same time, the brightening is frequently too slow. In addition, the dyes that are available in the state of the art have an inadequate service life and, hence, permit only negligible durability in ophthalmic sunglass lenses. The latter becomes noticeable in the rapid decrease in performance and/or in severe yellowing.

SUMMARY OF THE INVENTION

Therefore, the object of the present invention is to provide a class of photochromic compounds, which—limited to systems with a two atom bridge—are to have significantly improved properties in comparison to the structures described in the state of the art.

A further object of the invention is to provide a class of photochromic compounds which exhibit the combination of a long wave absorption maximum, a high darkening rate, a very fast brightening reaction, and a very good light stability.

These and other objects are achieved by the invention as described and claimed hereinafter. In particular, photochromic spirodihydrophenanthropyrans corresponding to formula I are provided:

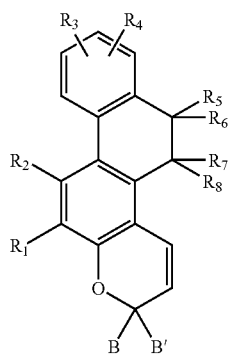

wherein
$R_1$, $R_2$, $R_3$ and $R_4$ each independently represent a substituent, selected from group α, consisting of hydrogen; $(C_1-C_6)$-alkyl; $(C_1-C_6)$-thioalkyl; $(C_3-C_7)$-cycloalkyl, which optionally may include one or more heteroatoms such as or S; $(C_1-C_6)$-alkoxy; hydroxyl; trifluoromethyl; bromine; chlorine; fluorine; unsubstituted, monosubstituted or disubstituted phenyl, phenoxy; benzyl, benzyloxy, naphthyl or naphthoxy; wherein the substituents in turn may be selected from the group α; or $R_1$ and $R_2$ and/or $R_3$ and $R_4$ independently form a -A-$(CH_2)_k$-D group or -A-$(C(CH_3)_2)_k$-D group, which is bonded to the aromatic ring, and wherein k=1 or 2, and A and D are independently selected from the group consisting of oxygen, sulfur, $CH_2$, $C(CH_3)_2$ and $C(C_6H_5)_2$, and wherein a benzo ring optionally may be annellated to said -A-$(CH_2)_k$-D group; or $R_1$ and $R_2$ and/or $R_3$ and $R_4$ independently represent an unsubstituted, monosubstituted, or disubstituted benzo or pyrido ring, which is annellated to the phenanthrene unit, and wherein the substituents may be selected from the group α;

$R_5$ and $R_6$ and/or $R_7$ and $R_8$ are selected, each independently of one another, from the group α, with the proviso that either $R_5$ and $R_6$, or $R_7$ and $R_8$, together with the spiro carbon atom to which they are attached form a 3 to 8 membered carbocyclic or heteromonocyclic spiro ring, which optionally may carry one or more substituents selected from the group α, and to which one to three aromatic or heteroaromatic ring systems optionally may be annellated, wherein said ring systems are independently selected from the group β, consisting of benzene, naphthalene, phenanthrene, pyridine, quinoline, furan, thiophene, pyrrol, benzofuran, benzothiophene, indol and carbazol, which in turn optionally may be substituted with one or more substituents selected from the group α, and wherein two vicinal annellated ring systems optionally may also be linked together by an ortho, ortho'bridge, or with the proviso that either $R_5$ and $R_6$ and/or $R_7$ and $R_8$ together with the spiro carbon atom to which they are attached form a 7 to 12 membered carbo-bicyclic spiro ring or a 7 to 12 membered carbo-tricyclic spiro ring, each of which optionally may carry one or more substituents selected from the group α, B and B' are independently selected from the following groups a), b) and c), wherein
a) consists of mono-, di- and trisubstituted aryl groups selected from the group consisting of phenyl, naphthyl and phenanthryl;
b) consists of unsubstituted, monosubstituted and disubstituted heteroaryl groups selected from the group consisting of pyridyl, furanyl, benzofuranyl, thienyl, benzothienyl, 1,2,3,4-tetrahydrocarbazolyl and julolidinyl;

wherein the substituents of the aryl or heteroaryl groups in a) and b) are selected from the group α or from the group χ, consisting of hydroxyl; 2-phenylethenyl which is unsubstituted, monosubstituted or disubstituted at the phenyl ring; (phenylimino)methylene which is unsubstituted, monosubstituted or disubstituted at the phenyl ring; (phenylmethylene)imino which is unsubstituted, monosubstituted or disubstituted at the phenyl ring; amino; mono-$(C_1-C_6)$ alkylamino; di-$(C_1-C_6)$-alkylamino; mono and diphenylamino which are unsubstituted, monosubstituted or disubstituted at the phenyl ring; piperidinyl; N-substituted piperzinyl; pyrrolidinyl; imidazolidinyl; pyrazolidinyl; indolinyl; morpholinyl; 2,6-dimethylmorpholinyl; thiomorpholinyl; azacycloheptyl; azacycloctyl; unsubstituted, monosubstituted or disubstituted phenothiazinyl; unsubstituted, monosubstituted or disubstituted phenoxazinyl; unsubstituted, monosubstituted or disubstituted 1,2,3,4-tetrahydroquinolinyl; unsubstituted, monosubstituted or disubstituted 2,3-dihydro-1,4-benzoxazinyl; unsubstituted, monosubstituted or disubstituted 1,2,3,4-tetrahydroisoquinolinyl; unsubstituted, monosubstituted or disubstituted phenazinyl; unsubstituted, monosubstituted or disubstituted carbazolyl; unsubstituted, monosubstituted or disubstituted 1,2,3,4-tetrahydrocarbazolyl; and unsubstituted, monosubstituted or disubstituted 10,11-dihydrodibenz[b,f]azepinyl; wherein the substituent(s) may in turn be independently selected from the group consisting of $(C_1-C_6)$-alkyl, $(C_1-C_6)$-alkoxy, bromine, chlorine, and fluorine; or wherein two directly vicinal substituents represent a Y—$(CX_2)_p$—Z grouping, where p=1, 2 or 3; X may be hydrogen, $CH_3$, or $C_6H_5$, and Y and Z each independently represent oxygen, sulfur, $N(C_1-C_6)$-alkyl, N—$C_6H_5$, $CH_2$, $C(CH_3)_2$, or $C(C_6H_5)_2$, wherein two or more adjacent carbon atoms of this Y—$(CX_2)_p$—Z grouping may be, each independently of one another, also part of a benzo ring system, which is annellated thereto and each of which in turn optionally may carry one or more substituents, selected from the group α or the group χ;
or
c) B and B' together with the adjacent carbon atom of the pyran ring form an unsubstituted, monosubstituted or disubstituted 9,10-dihydroanthracene, fluorene, thioanthene, xanthene, benzo[b]fluorene, 5H-dibenzo[a,d]cycloheptene or dibenzosuberone group or a saturated hydrocarbon group, which is $(C_3-C_{12})$ spiro monocyclic, $(C_7-C_{12})$ spiro bicyclic and/or $(C_7-C_{12})$ spiro tricyclic, wherein the substituents of the unsaturated cycles are each independently selected from the group α or the group χ.

In contrast to the two atom bridge systems that are currently available in the state of the art, the photochromic compounds of the present invention, which are derived from spirodihydrophenanthropyrans, exhibit a significantly improved property profile, in particular an improved combination of very good service life as well as a faster brightening rate. In addition, in contrast to compounds having a one atom bridge, the compounds of the invention exhibit not only a faster brightening rate but also a lower solvatochromy. The compounds of the invention exhibit a good balance between long wave absorption maximum, high darkening rate, very fast brightening reaction and very good light stability.

Preferred photochromic spirodihydrophenanthropyrans, according to the present invention correspond to the following formula II:

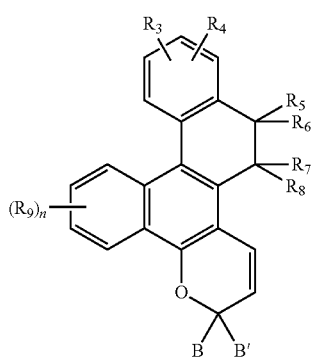

II wherein
B, B', $R_3$, $R_4$, $R_5$, $R_6$, $R_7$, and $R_8$ are defined as above;
$R_9$ is selected from the group α; and
n is 0, 1, 2, 3, or 4.

According to the invention, either $R_5$ and $R_6$ together or $R_7$ and $R_8$ together with the Spiro carbon atom to which they are attached form a 3 to 8 membered carbocyclic or heteromonocyclic spiro ring and/or a 7 to 12 membered carbo bicyclic spiro ring or a 7 to 12 membered carbo tricyclic spiro ring, as defined above. However, it is also possible for both $R_5$ and $R_6$ and also $R_7$ and $R_8$, each together with the spiro carbon atom to which they are attached, to form respectively a 3 to 8 membered carbocyclic or heteromonocyclic spiro ring and/or a 7 to 12 membered carbo bicyclic spiro ring or a 7 to 12 membered carbo tricyclic spiro ring, so that then there are two spiro cyclic rings in positions 9 and 10.

The $C_7$-$C_{12}$ spiro bicyclic systems are well-known to persons skilled in the art. Some examples which may be mentioned include norbornane, norbornene, 2,5-norbornadiene, norcaran and pinan. A known $C_7$-$C_{12}$ spiro tricyclic system is, for example, adamantane.

Preferably $R_7$ and $R_8$ together with the spiro carbon atom to which they are attached form a 3 to 8 membered carbocyclic or heterocyclic ring, to which one to three aromatic or heteroaromatic ring systems may be annellated. In this case the ring system is selected from the group β, consisting of benzene, naphthalene, phenanthrene, pyridine, quinoline, furan, thiophene, pyrrol, benzofuran, benzothiophene, indol and carbazol, which in turn may be substituted with one or more substituents selected from the group α. In this case, two vicinal annellated ring systems may also be linked together by an ortho, ortho' bridge, preferably an ethylene bridge or a 1,2-ethenediyl bridge, so that, for example, in the latter case there is the following structural unit—that is, a spiro-(phenanthrene-4,5-diyl) unit.

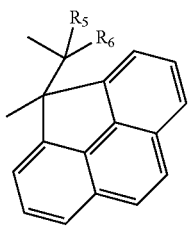

If B and/or B' represents or represent a saturated hydrocarbon which is $C_3$-$C_{12}$ spiro monocyclic, $C_7$-$C_{12}$ spiro bicyclic or $C_7$-$C_{12}$ spiro tricyclic, then $C_3$-$C_{12}$ spiro monocyclic is defined as a 3 membered to 12 membered ring, with which the person skilled in the art is familiar. Even $C_7$-$C_{12}$ spiro bicyclic systems are well-known to persons skilled in the art. Examples which can be mentioned include norbornane, norbornene, 2,5-norbornadiene, norcaran and pinan. A known $C_7$-$C_{12}$ spiro tricyclic system is, for example, adamantane.

In one preferred embodiment, $R_7$ and $R_8$ together with the spiro carbon atom to which they are attached represent a 5 to 7 membered carbo monocyclic ring, which in turn optionally may carry one, two, three or four substituents selected from the group α. In this case one to three benzo rings may be annellated to the carbocyclic ring. These benzo rings in turn optionally may carry one or two substituents, selected from the group α.

In another preferred embodiment $R_7$ and $R_8$ together with the spiro carbon atom to which they are attached represent a 7 to 8 membered carbo bicyclic ring (that is, a bicycloheptane or bicyclooctane ring system) and/or an adamantyl ring, each of which in turn optionally may carry one, two, three or four substituents selected from the group α.

In another preferred embodiment B and B' are independently selected from the group a) as defined above.

The substituents of the group χ, which comprise nitrogen atoms and/or carry amine groups, are bonded through these nitrogen atoms or amine groups to the phenyl, naphthyl and/or phenanthryl group of the group α.

If with respect to the substituents of the group χ, which may be bonded to the phenyl, naphthyl or phenanthryl moiety of group a) for B and/or B', two or more adjacent carbon atoms of this Y—$(CX_2)_p$—Z grouping may each independently of one another be a part of a benzo ring system that is annellated thereto, then this means that then the two methylene carbon atoms (—$CH_2$—$CH_2$—) are a part of an annellated ring system. If, for example, two or three benzo rings are annellated, then, for example, the following structural units may exist, as shown below.

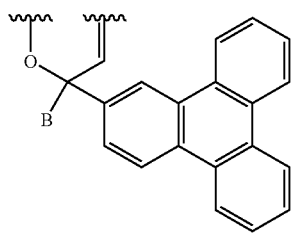

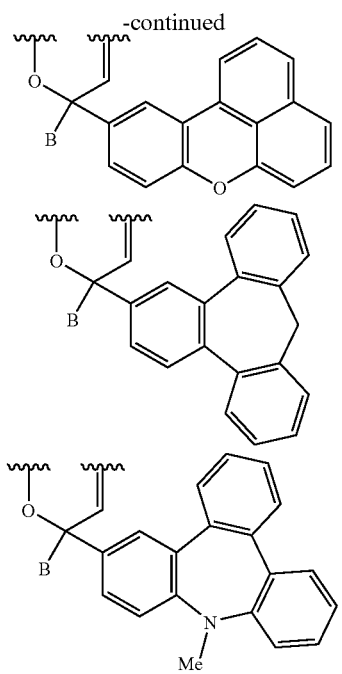

-continued

However, it is also possible that there exists only one benzo ring, which is annellated via two adjacent carbon atoms of this Y—$(CX_2)_p$—Z group.

The compounds according to the invention may be used in plastic materials and/or plastic objects of any type and/or shape for a variety of purposes for which the photochromic behavior is of importance. Moreover, a single dye according to the present invention or a mixture of such dyes may be used. For example, the photochromic spirodihydrophenanthropyran dyes of the invention may be used in lenses, in particular ophthalmic lenses, lenses for spectacles of all types, such as ski goggles, sunglasses, motorcycle goggles, visors of helmets and the like. Moreover, the photochromic spirodihydrophenanthropyrans of the invention also may be used, for example, as solar protection in vehicles and residences in the form of windows, protective shutters, coverings, roofs or the like.

To prepare such photochromic objects, the photochromic spirodihydrophenanthropyrans of the invention can be applied to or embedded within a polymer material, such as an organic synthetic resin material, by various methods know in the art, such as those already disclosed in WO 99/15518.

In this respect a distinction is made between mass dyeing methods and surface dyeing methods. A mass dyeing method comprises, for example, the dissolution or dispersion of the photochromic compound or compounds, according to the present invention, in a plastic material, for example, by the addition of the photochromic compound(s) to a monomeric material, before polymerization takes place. Another possibility of producing a photochromic object is the penetration of the plastic material(s) with the photochromic compound(s) by immersion of the plastic material in a hot solution of the photochromic dye(s) of the present invention or, for example, by a thermo transfer method. The photochromic compound(s) may also be provided, for example, in the form of a separate layer between contiguous layers of the plastic material, such as a part of a polymer film. Furthermore, it is also possible to apply the photochromic compound(s) as part of a coating applied to the surface of the plastic material. In this context, the expression "penetration" is intended to mean the migration of the photochromic compound(s) into the plastic material, for example, by the solvent-assisted transfer of the photochromic compound(s) into a polymer matrix, by the vapor phase transfer or by any other process of surface diffusion of this type.

The photochromic objects, such as spectacle lenses, can be produced advantageously not only by means of the conventional mass dyeing process but also just as well by means of surface dyeing, with the latter variant being suitable to achieve a surprisingly reduced migration tendency. This feature is especially advantageous in the subsequent processing steps, since, for example in the case of an anti-reflection coating the lower back-diffusion under vacuum causes significantly less detachment of the layers and similar defects.

On the whole, on the basis of the inventive photochromic spirodihydrophenanthropyrans, any dyes—that is, dyes, which are compatible (from a chemical and color point of view)—may be applied to or embedded within the synthetic resin material in order to satisfy both an esthetic aspect as well as medical or fashion factors. Consequently the specifically selected dye or dyes may vary as a function of the intended effects and requirements.

BRIEF DESCRIPTION OF THE DRAWING

The accompanying drawing FIGURE is a depiction of an example reaction scheme for synthesizing the compounds of the invention.

SYNTHESIS DESCRIPTION

The photochromic compounds of the invention can be synthesized by a known method (cf. WO 02/22594) by reacting suitably substituted spirodihydrophenanthrene derivatives with suitably substituted 2-propin-1-ol derivatives. The production of the inventive compounds is explained below by a general reaction scheme as an example (see FIG. 1).

In a first step suitably substituted methylidene succinanhydrides are subjected to a Friedel Crafts reaction with suitably substituted 1,2-ethylenes (step (i)). The —COOH group of the resulting intermediate is then protected; and this intermediate is subjected to a cuprate-assisted Michael addition with correspondingly substituted benzyl derivatives (step (ii)). After removal of the carboxylic acid protective group, correspondingly substituted spirodihydrophenanthrene derivatives are formed via intramolecular cyclization by means of phosphoric acid (step (iii)). Then, these substituted spirodihydrophenanthrene derivatives are reacted with suitably substituted 2-propin-1-ol derivatives, according to step (iv), to form the compounds of the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A photochromic spirodihydrophenanthropyran compound corresponding to formula I:

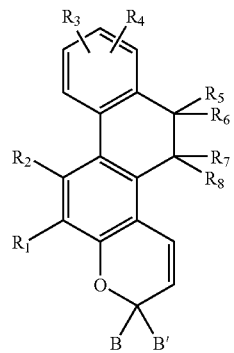

wherein $R_1$, $R_2$, $R_3$ and $R_4$ each independently represent a substituent, selected from the group α, consisting of hydrogen; $(C_1-C_6)$-alkyl; $(C_1-C_6)$-thioalkyl; $(C_3-C_7)$-cycloalkyl which optionally may contain one or more heteroatoms; $(C_1-C_6)$-alkoxy; hydroxyl; trifluoromethyl; bromine; chlorine; fluorine; and unsubstituted, monosubstituted or disubstituted phenyl, phenoxy, benzyl, benzyloxy, naphthyl or naphthoxy, wherein the substituents are selected from the group α; or $R_1$ and $R_2$, or $R_3$ and $R_4$, or both, form a -A-$(CH_2)_k$-D group or -A-$(C(CH_3)_2)_k$-D group bonded to the aromatic ring and wherein k=1 or 2, and A and D are independently selected from the group consisting of oxygen, sulfur, $CH_2$, $C(CH_3)_2$ and $C(C_6H_5)_2$, and wherein the -A-$(CH_2)_k$-D group optionally may have a benzo ring annellated thereto; or $R_1$ and $R_2$, or $R_3$ and $R_4$, or both, independently represent an unsubstituted, monosubstituted, or disubstituted benzo or pyrido ring, which is annellated to the phenanthrene unit, wherein the substituents are selected from the group α;

$R_5$ and $R_6$, or $R_7$ and $R_8$, or both, are independently selected from the group α, with the proviso that either $R_5$ and $R_6$, or $R_7$ and $R_8$, together with the spiro carbon atom to which they are attached form a 3 to 8 membered carbocyclic or heteromonocyclic spiro ring, which optionally may carry one or more substituents selected from the group α, and to which one to three aromatic or heteroaromatic ring systems optionally may be annellated, wherein the ring systems are independently selected from the group β, consisting of benzene, naphthalene, phenanthrene, pyridine, quinoline, furan, thiophene, pyrrol, benzofuran, benzothiophene, indol and carbazol, wherein said ring systems optionally may be substituted with one or more substituents selected from the group α, and wherein two vicinal annellated ring systems optionally may also be linked together by an ortho, ortho' bridge, or with the proviso that either $R_5$ and $R_6$, or $R_7$ and $R_8$, or both, together with the spiro carbon atom to which they are attached form a 7 to 12 membered carbobicyclic spiro ring or a 7 to 12 membered carbotricyclic spiro ring, each of which optionally may carry one or more substituents selected from the group α, B and B' are independently selected from following groups a), b) and c), wherein a) consists of mono-, di- and trisubstituted aryl groups selected from the group consisting of phenyl, naphthyl and phenanthryl;

b) consists of unsubstituted, monosubstituted and disubstituted heteroaryl groups selected from the group consisting of pyridyl, furanyl, benzofuranyl, thienyl, benzothienyl, 1,2,3,4-tetrahydrocarbazolyl and julolidinyl; wherein the substituents of the aryl or heteroaryl groups in a) and b) are selected from the group α or the group χ, consisting of hydroxyl; 2-phenylethenyl which is unsubstituted, monosubstituted or disubstituted at the phenyl ring; (phenylimino)methylene which is unsubstituted, monosubstituted or disubstituted at the phenyl ring; (phenylmethylene)imino which is unsubstituted, monosubstituted or disubstituted at the phenyl ring; amino; mono-$(C_1-C_6)$-alkylamino; di-$(C_1-C_6)$ alkylamino; mono and diphenylamino which are unsubstituted, monosubstituted or disubstituted at the phenyl ring; piperidinyl; N-substituted piperzinyl; pyrrolidinyl; imidazolidinyl; pyrazolidinyl; indolinyl; morpholinyl; 2,6-dimethylmorpholinyl; thiomorpholinyl; azacycloheptyl; azacyclooctyl; unsubstituted, monosubstituted or disubstituted phenothiazinyl; unsubstituted, monosubstituted or disubstituted phenoxazinyl; unsubstituted, monosubstituted or disubstituted 1,2,3,4-tetrahydroquinolinyl; unsubstituted, mono-substituted or disubstituted 2,3-dihydro-1,4-benzoxazinyl; unsubstituted, monosubstituted or disubstituted 1,2,3,4-tetrahydroisoquinolinyl; unsubstituted, monosubstituted or disubstituted phenazinyl; unsubstituted, monosubstituted or disubstituted carbazolyl; unsubstituted, monosubstituted or disubstituted 1,2,3,4-tetrahydrocarbazolyl; and unsubstituted, monosubstituted or disubstituted 10,11-dihydrodibenz[b,f]azepinyl; wherein the substituent(s) are independently selected from the group consisting of $(C_1-C_6)$-alkyl, $(C_1-C_6)$-alkoxy, bromine, chlorine, and fluorine; or wherein two directly vicinal substituents represent a Y—$(CX_2)_p$—Z grouping, where p=1, 2 or 3; X represents hydrogen, $CH_3$, or $C_6H_5$, and Y and Z each independently represent oxygen, sulfur, $N(C_1-C_6)$-alkyl, N—$C_6H_5$, $CH_2$, $C(CH_3)_2$, or $C(C_6H_5)_2$, wherein two or more adjacent carbon atoms of this Y—$(CX_2)_p$—Z grouping may be, each independently of one another, also part of a benzo ring system, which is annellated thereto and each of which in turn optionally may carry one or more substituents, selected from the group α or the group χ; or c) B and B' together with the adjacent carbon atom of the pyran ring form an unsubstituted, monosubstituted or disubstituted 9,10-dihydroanthracene, fluorene, thioanthene, xanthene, benzo[b]fluorene, 5H-dibenzo[a,d]cycloheptene or dibenzosuberone group or a saturated hydrocarbon group which is $(C_3-C_{12})$ spiro monocyclic, $(C_7-C_{12})$ spiro bicyclic or $(C_7-C_{12})$ spiro tricyclic, wherein the substituents of the unsaturated cycles are independently selected from the group α or the group χ.

2. A photochromic spirodihydrophenanthropyran compound as claimed in claim 1, wherein said compound corresponds to formula II:

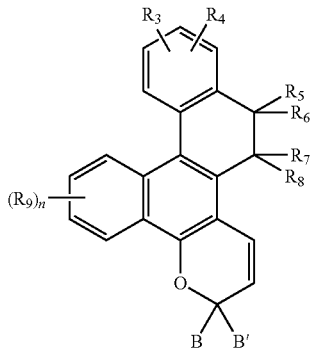

wherein

B, B', $R_3$, $R_4$, $R_5$, $R_6$, $R_7$, and $R_8$ are defined as in claim 1;
$R_9$ is selected from the group a; and
n is 0, 1, 2, 3, or 4.

3. A photochromic spirodihydrophenanthropyran compound as claimed in claim 1, wherein $R_7$ and $R_8$ together with the spiro carbon atom to which they are attached form a 3 to 8 membered carbocyclic or heterocyclic ring, to which one to three aromatic or heteroaromatic ring systems may be annellated, wherein said ring systems are selected from the group β consisting of benzene, naphthalene, phenanthrene, pyridine, quinoline, furan, thiophene, pyrrol, benzofuran, benzothiophene, indol and carbazol; wherein said ring systems optionally may be substituted with one or more substituents selected from the group α, and wherein two vicinal annellated ring systems optionally may be linked together by an ortho, ortho' bridge.

4. A photochromic spirodihydrophenanthropyran compound as claimed in claim 3, wherein two vicinal annellated ring systems are linked by an ethylene bridge or a 1,2-ethenediyl bridge.

5. A photochromic spirodihydrophenanthropyran compound as claimed in claim 1, wherein $R_7$ and $R_8$ together with the spiro carbon atom to which they are attached represent a 5 to 7 membered carbo monocyclic ring, which optionally may carry one, two, three or four substituents selected from the group α; wherein one to three benzo rings may be annellated to the carbocyclic ring; and wherein said benzo rings optionally may carry one or two substituents, selected from the group α.

6. A photochromic spirodihydrophenanthropyran compound as claimed in claim 1, wherein $R_7$ and $R_8$ together with the spiro carbon atom to which they are attached represent a 7 to 8 membered carbo bicyclic ring or an adamantyl ring, each of which in turn optionally may carry one, two, three or four substituents selected from the group α.

7. A photochromic spirodihydrophenanthropyran compound as claimed in claim 1, wherein B and B' are independently selected from the group α.

8. A photochromic synthetic resin article comprising a synthetic resin body having a photochromic spirodihydrophenanthropyran compound as claimed in claim 1 applied thereto or embedded therein.

9. A photochromic synthetic resin article as claimed in claim 8, wherein said synthetic resin body is an ophthalmic lens.

* * * * *